US007846130B2

(12) United States Patent
Elazari-Volcani et al.

(10) Patent No.: US 7,846,130 B2
(45) Date of Patent: Dec. 7, 2010

(54) PORTABLE INTRAVENOUS FLUID HEATING SYSTEM

(75) Inventors: Ron Elazari-Volcani, Rehovot (IL); David Vishnia, Raanana (IL); Eyal Shani, Gan Yeshaya (IL)

(73) Assignee: Quality in Flow Ltd., Petach Tikva (IL)

( * ) Notice: Subject to any disclaimer, the term of this patent is extended or adjusted under 35 U.S.C. 154(b) by 197 days.

(21) Appl. No.: 11/685,234

(22) Filed: Mar. 13, 2007

(65) Prior Publication Data

US 2008/0228142 A1 Sep. 18, 2008

(51) Int. Cl.
*A61F 7/12* (2006.01)

(52) U.S. Cl. ........................................................ 604/114

(58) Field of Classification Search .................. 604/114
See application file for complete search history.

(56) References Cited

U.S. PATENT DOCUMENTS

| | | | | |
|---|---|---|---|---|
| 1,995,302 | A | | 3/1935 | Goldstein |
| 3,355,572 | A | | 11/1967 | Chow |
| 4,038,519 | A | * | 7/1977 | Foucras ...................... 392/472 |
| 4,707,587 | A | * | 11/1987 | Greenblatt .................. 392/466 |
| 5,106,373 | A | | 4/1992 | Augustine et al. |
| 5,713,864 | A | | 2/1998 | Verkaart |
| 6,139,528 | A | | 10/2000 | Kistner et al. |
| 6,142,974 | A | * | 11/2000 | Kistner et al. ............... 604/113 |
| 6,480,257 | B2 | | 11/2002 | Cassidy et al. |
| 6,974,463 | B2 | | 12/2005 | Magers et al. |
| 7,158,719 | B2 | | 1/2007 | Cassidy |
| 7,377,148 | B2 | | 5/2008 | Cassidy |
| 7,547,295 | B2 | | 6/2009 | Cassidy |
| 7,695,448 | B2 | | 4/2010 | Cassidy et al. |
| 2008/0077087 | A1 | * | 3/2008 | Martens ...................... 604/113 |

FOREIGN PATENT DOCUMENTS

| | | |
|---|---|---|
| GB | 1488156 | 10/1977 |
| WO | WO2006102260 | 9/2006 |
| WO | WO2008111084 | 9/2008 |

* cited by examiner

*Primary Examiner*—Nicholas D Lucchesi
*Assistant Examiner*—Jason Flick
(74) *Attorney, Agent, or Firm*—Mark M. Friedman

(57) ABSTRACT

The present invention discloses a portable intravenous fluid heating system comprising (a) a metallic heated conduit for warming IV fluids passed therethrough at a continuously regulated normal body temperature and transporting said IV fluids; and, (b) a controller unit including a power source operative to apply an electric potential across said conduit. The conduit comprises a wall made of a metallic material capable of producing resistance heat by the passage of electric current, such that said IV fluid is heated by the contact with said wall.

11 Claims, 5 Drawing Sheets

12
16
102
100
104
18
14
Body

PORTABLE INTRAVENOUS FLUID HEATING SYSTEM

FIELD OF THE INVENTION

The present invention generally relates to a portable intravenous fluid heating system. More specifically, the present invention relates to a portable heating fluid system, stable under extreme environment conditions transporting and warming any IV fluid infusion at a continuously regulated body temperature.

BACKGROUND OF THE INVENTION

By way of introduction, fluids that are administered intravenously to a patient include blood-based fluids and non-blood fluids, collectively referred to as "intravenous (IV) fluids" herein. While awaiting use, blood-based fluids are maintained in cool storage at approximately 4° C. Non-blood fluids are usually stored at room-temperature.

Moreover, in extreme environmental conditions when the body is exposed to colder temperatures, its internal mechanisms may be unable to replenish the heat that is being lost to the body's surroundings. It is well known that hypothermia poses a significant peril to emergency patients. Intravenous administration of unheated IV fluids, having the extreme environmental temperature, in such patients can cause substantial heat loss and can cause, or at least contribute to, serious patient hypothermia problems and hence aggravate the patient condition.

In the art, it is known to warm IV fluids prior to intravenous administration. However, care must be exercised: overheating IV fluids, especially blood-based compositions, could destroy cells, and endangers the patient life. Examples of method and convection systems for heating IV fluids are disclosed in U.S. Pat. Nos. 4,707,587 and 5,106,373. A heat exchanger may also be employed for keeping the temperature of the IV fluid constant. Unfortunately, this possesses the disadvantage of requiring a large amount of fluid and of increasing the overall size of the apparatus. It is also possible to surround medical tube for carrying and heating the IV fluid with heating elements. It is noted that such heating fluid systems have been described in several patent documents, including U.S. Pat. Nos. 1,995,302; 4,038,519; and 3,355,572 each of which is incorporated by reference in its entirety U.S. Pat. Nos. 1,995,302 and 4,038,519 feature a flexible tube suitable for medical uses in which heating is provided by means of wires or strips of a resistance heating conductor embedded in a helical fashion within the walls of the tubing. U.S. Pat. No. 3,355,572 discloses composite tubing in which heating wires are wound spirally around the inner layer of the tubing and are embedded in the outer layer of the tubing.

While some of the above-mentioned devices are appropriate for their particular uses, they tend to heat in a linear or local manner, resulting in local overheating of the fluid in the conduit. This effect is inconsequential in many applications. A problem arises, however, when heating an IV fluid, such as blood, because it begins to degrade at temperatures of about 45.5° C. Because blood must be heated to regulated normal body temperature (about 37° C.) to achieve optimal results, the conduit must be capable of heating blood uniformly and maintaining its temperature within a narrow range. Another shortcoming of the above-mentioned devices is the inability to accurately monitor the fluid temperature, due to the incapacity of accurately controlling the heat dissipated by heating wires or strips.

Moreover, in order for a bulk warmer to be constantly ready for emergency use, it must be maintained at a proper and set temperature. This requires a system which is bulky, heavy, and/or fixed. The use is impracticable under field emergency conditions, in situations such as military field conditions, pre-hospital such as flight or ambulance conditions or outpatients environment conditions.

U.S. Pat. No. 6,142,974 to Kistner et al. discloses a tube network containing parallel straight sections in the same plane, wrapped in a flexible material which supports resistance heater elements. Unfortunately, in the above-mentioned system fluid leakage often occurs due to the discontinuity of the conduit.

Therefore, there is an ongoing need for a portable safe heating fluid system, stable wider extreme environment conditions transporting and warming any IV fluid infusion at a continuously regulated body temperature, thereby preventing hypothermia.

SUMMARY OF THE INVENTION

It is thus provided a novel portable intravenous fluid heating system including a metallic heated conduit for warming IV fluids passed therethrough at a continuously regulated normal body temperature and transporting the IV fluids; and a controller unit including a power source operative to apply an electric potential across the conduit.

Preferably, the controller unit includes a monitor operative to regulate the temperature of the fluid flowing inside the conduit having high precision in the range of about 0.1° C. to about 0.3° C. at a flow rate of about 2 to about 60 ml/min. The monitor includes at least one sensor adapted to measure the fluid flow temperature. The monitor regulates the temperature of the conduit.

According to another embodiment of the present invention the monitor regulates the temperature of the fluids Preferably, the sensor is placed inside the fluid path.

According to one embodiment of the present invention, the thickness of the conduit is configured such that the temperature of the external surface of the conduit is almost identical to the temperature of the internal surface conduit.

According to another embodiment of the present invention, the controller unit further includes an electric circuit including: a sensor for determining the temperature selected from the group including the temperature of the fluid heated by the conduit and the temperature of the conduit; and, an interrupter.

Preferably, the system further includes a first connector means for receiving unwarmed fluid; and a second connector means for continuously delivering fluid at a continuously regulated normal body temperature. Preferably, the conduit is formed from stainless steel.

According to one embodiment of the present invention, the system is lightweight. Preferably, the system is activated under a low voltage of about 6V to about 24V.

According to another embodiment of the present invention, the system is adapted to be utilized in field environment selected from the group consisting of emergency medical services, flight or watercraft service, military field, excursion field, and sport field. Preferably, the system is stored at temperatures between −20° C. to 40° C.

There is also provided a metallic heated conduit for warming and transporting IV fluids at a continuously regulated body temperature; the conduit including a wall made of a metallic material capable of producing resistance heat by the passage of electric current, such that the IV fluid is heated by the contact with the wall. Preferably, the conduit is formed from stainless steel. The thickness of the conduit is configured such that the temperature of the fluid flow is almost identical to the temperature of the conduit.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide an intravenous fluid heating system.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The term 'plurality' applies hereinafter to any integer greater than or equal to one.

The term 'about' refers hereinafter, to a tolerance of ±20% of the defined measure.

The term 'regulated normal body temperature' refers hereinafter to the body temperature of about 37° C.

The term 'sensor' refers hereinafter to any temperature sensors configured to measure the temperature of a predetermined location and to display the temperature selected from the group consisting of thermometers, thermocouples, temperature sensitive resistors (thermistors and resistance temperature detectors) and bi-metal thermometers.

The term 'monitor' refers hereinafter to a device configured to regulate the sensed temperature of a system so that the system's temperature is maintained near a desired set point temperature, such as a thermostat. The regulation comprises comparing a measurement of the sensed temperature with a reference. Monitors can be constructed in many ways and may use a variety of sensors to measure the temperature.

Figure 1:
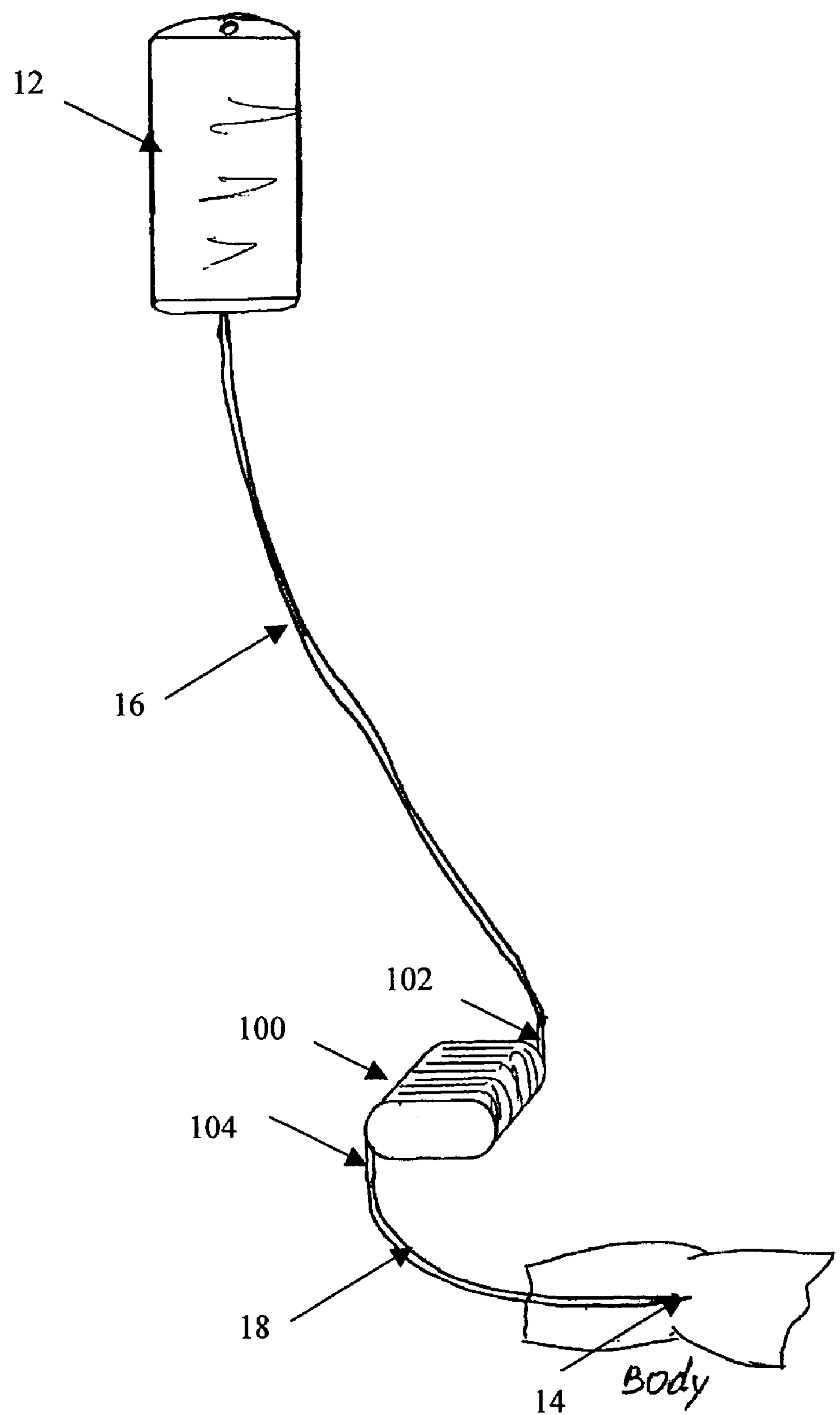
FIG. 1 is a schematic cross-sectional view of an intravenous fluid heating system showing the connection of the heating system to a tube which transports the IV unwarmed fluids from an infusion bag at one end, and at the other end to a tube which transports the IV warmed fluids to the patient's infusion point.

Reference is made now to FIG. 1 presenting a schematic and generalized illustration of the aforementioned novel portable heating system generally designated 100. Heating system 100 is connected via a first connector means 102 to a tube 16 which transports the IV unwarmed fluids from an infusion bag 12, and via a second connector means 104 to a tube 18 which transports the IV warmed fluids to the patient's infusion point 14. There is no limitation on the connector means, neither on the tube. System 100 is adapted to be connected to any commercially available infusion tube port.

Figure 2:
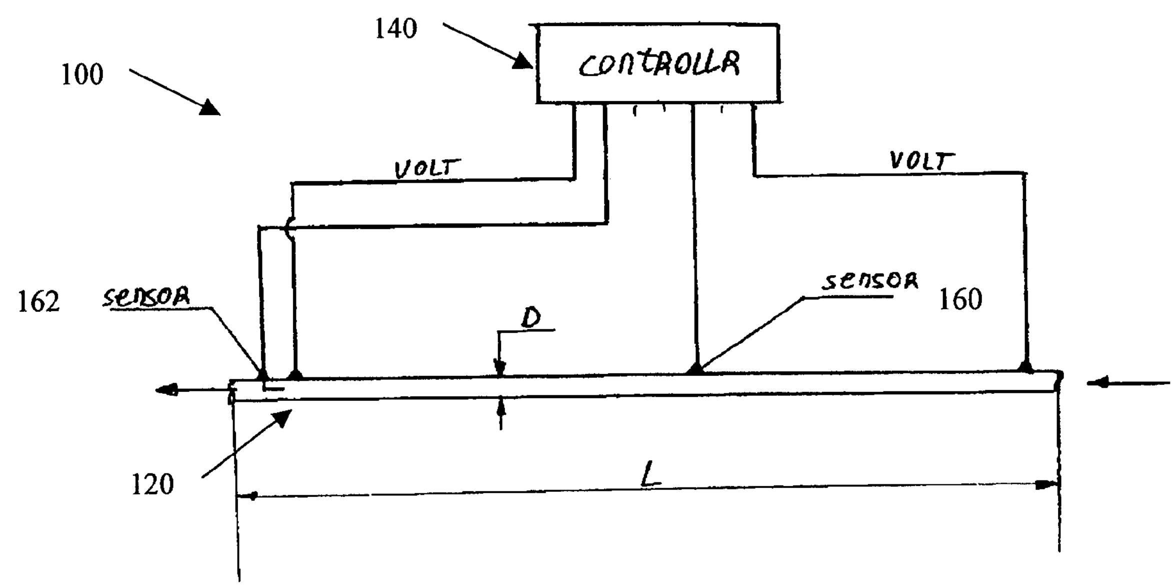
FIG. 2 is a schematic partial cross-sectional view of an intravenous fluid heating system showing two monitors and a controller unit for actuating and monitoring the fluid heating system.

Reference is made now to FIG. 2 presenting a schematic and generalized illustration of the aforementioned portable heating system 100. Heating system 100 includes a heated conduit 120 formed from a metallic material especially designed for warming and transporting IV fluids, and a controller unit 140 including a power source operative to heat one or more infusion bags (preferably two) from a temperature of about 4° C. to a regulated normal body temperature of about 37° C. Heated conduit 120 is operative as an ohmic heater when an electric potential is applied across it. An electric current is hence applied to the extremities of conduit 120. There is no limitation on the electrical power source. The power source may be a portable battery (such as a rechargeable battery), a vehicle/aircraft power supply or may include a rechargeable "capacitor." In one non-limiting example, the length L of conduit 120 is in the range of about 1 m to about 6 m, preferably in the range of about 3 m to about 5 m; the diameter of conduit 120 is in the range of about 0.8 mm to about 5 mm, preferably 2.8 mm and the depth D of the conduit wall is in the range of about 0.05 mm to about 0.4 mm, preferably in the range of about 0.1 mm to about 0.25 mm. The distance to the patient infusion point is about 5 cm to about 20 cm.

According to one embodiment of the present invention, controller unit 140 further includes a display screen for displaying the monitored temperatures.

According to one embodiment of the present invention, conduit 120 is coiled to reduce the packing size.

According to one embodiment of the present invention conduit 120 is a medical grade stainless steel tube. One of the advantages of this type of conduit is that it avoids some of the problems associated with thermal degradation. The term "thermal degradation": refers to an overheating of the conduit, due for example to the activation of the system including air instead of fluid, in which the conduit is able to be melted or to release unwanted substances into the IV fluids.

Moreover, conventionally available polymer tubes have an extremely low ability to transmit heat as defined by their respective thermal conductivity between 0.12 and 0.42 W/m*K while a conduit formed from a stainless steel tube having a higher thermal conductivity of about 9.42 W/m*K is a much better heat conductor.

Another advantage of this type of conduit is the durably stability of the material under extreme environmental conditions, sun radiation. Conduit 120 may also be stored in machine rooms without altering its stability.

The length and the thickness of metallic conduit 120 are especially designed to provide a continuous gradual uniform accurate heating as well as high energy efficiency throughout the internal surface of conduit 120. Due to the high thermal conductivity of conduit 120, the heat efficiency is provided by the transfer from the external surface of conduit 120 to its internal wall which is in direct contact with IV fluids. The high heat efficiency ensures low energy consumption. Therefore, the high energy efficiency is also provided because conduit 120 behaves as an ohmic heater, therefore the thermal energy is efficiently directly transferred from conduit 120 to the IV fluid.

According to another embodiment of the present invention, conduit 120 may be disposable and able to be disconnected from controller unit 140 and/or replaced in system 100.

According to another embodiment of the present invention, conduit 120 may be adapted to multiple uses.

Controller unit 140 also includes a monitor operative to measure the temperature of the fluid flowing inside conduit 120 having high precision of in the range of about 0.1 to about 0.3° C. at a flow rate of about 2 to about 60 ml/min. The monitor includes at least one sensor adapted to measure the fluid flow temperature. A monitor 160 deployed on the external surface of conduit 120 regulates the temperature of conduit 120. The thickness of conduit 120 is configured such that the temperature of the external surface of conduit 120 is almost identical to the temperature of the internal wall conduit 120. The term "almost" refers to a difference of about 0.1 to 0.5° C. This feature provides a highly accurate measurement, along the conduit length. Another monitor 162 regulates the temperature of the fluid before its introduction to the patient's infusion point.

Figure 3:
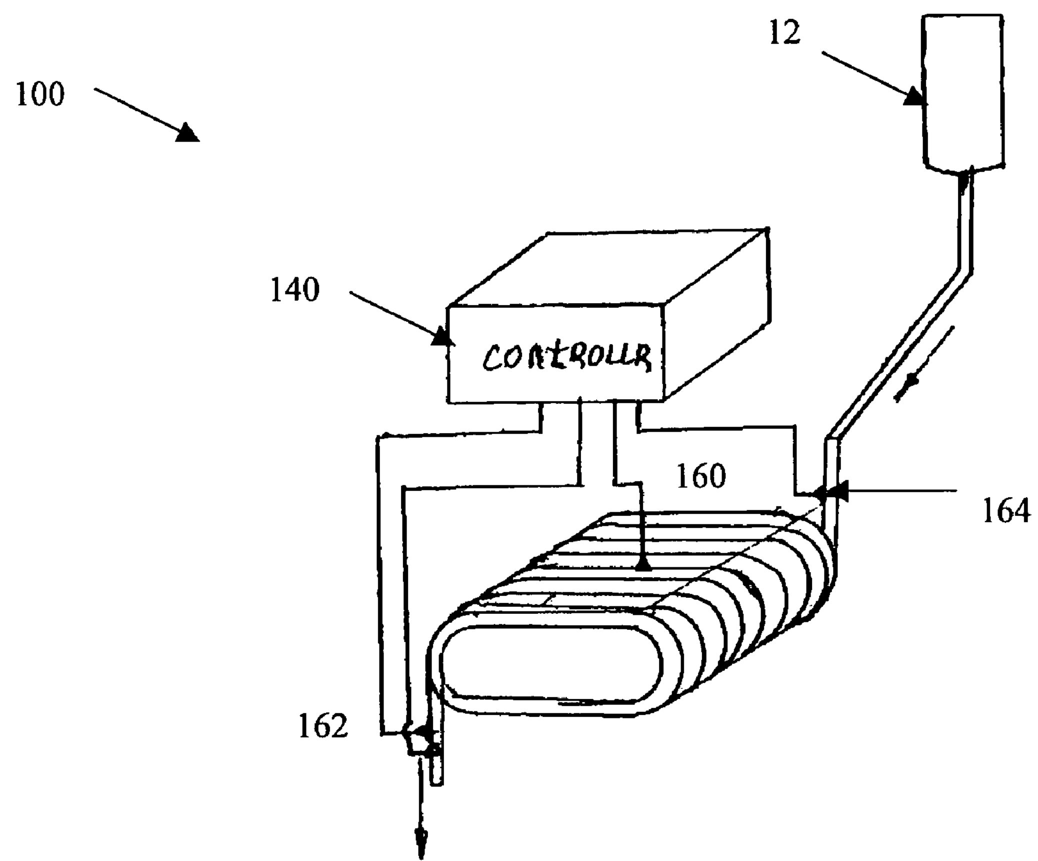
FIG. 3 is a schematic partial cross-sectional view of another configuration of an intravenous fluid heating system showing three monitors and a controller unit for actuating and monitoring the fluid heating system; and, FIG. 4 is a schematic partial cross-sectional view of another configuration of an intravenous fluid heating system showing a schematic electrical circuit for actuating and monitoring the fluid heating system; and, FIG. 5 is a schematic partial cross-sectional view of the heating conduit.

Reference is made now to FIG. 3 presenting another schematic and generalized illustration of the aforementioned portable heating system 100 in which a monitor 164 determines the temperature of the fluid before its introduction to system 100.

Figure 4:
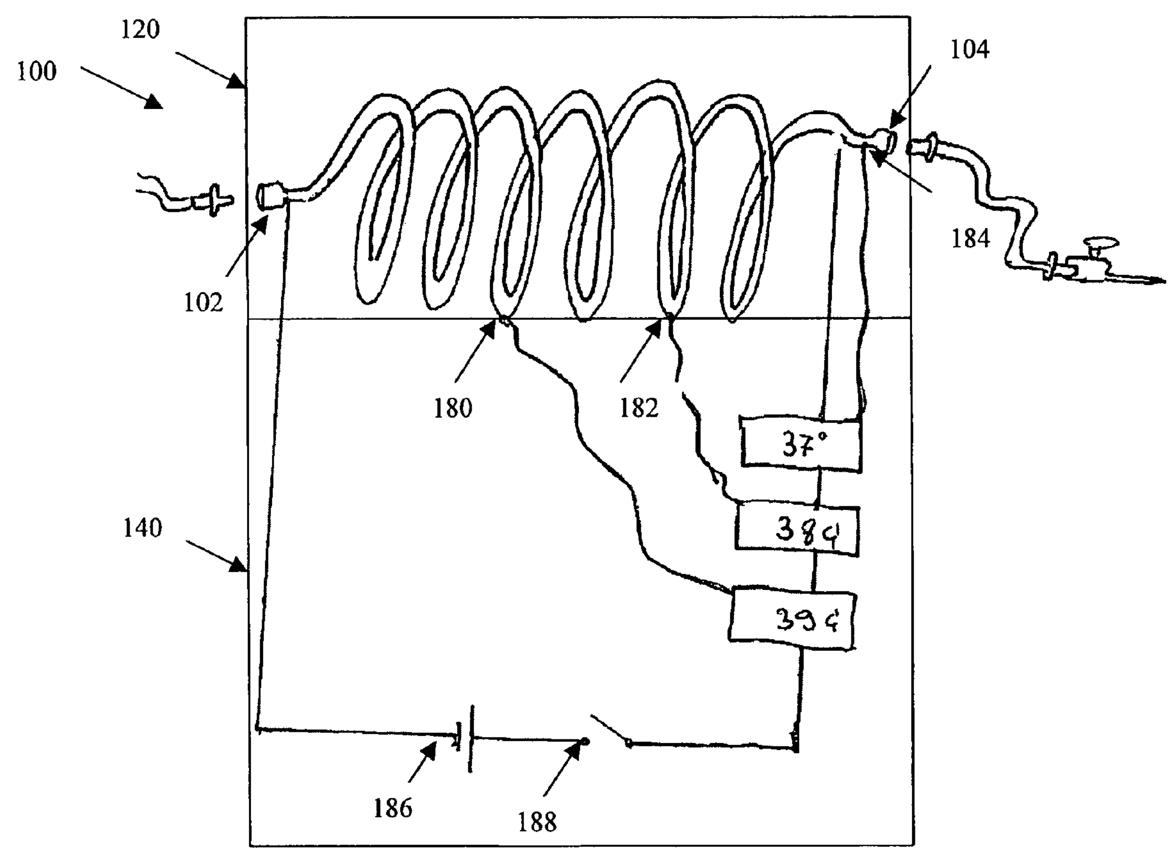

Reference is made now to FIG. 4 presenting another schematic and generalized illustration of the aforementioned portable heating system 100. Heating system 100 is connected via a first connector means 102 to a tube which transports the IV unwarmed fluids from an infusion bag, and via a second connector means 104 to a tube which transports the IV warmed fluids to the patient's infusion point. Controller unit 140 further includes an electric circuit including first and second sensors respectively 180 and 182 operative to measure the temperature throughout conduit 120; a power source 186 and an interrupter 188 for actuating and stopping the electrical circuit. For example, interrupter 188 stops the electrical input on conduit 120 when the temperature of conduit 120 and/or of the fluid has increased beyond certain predetermined value. Controller unit 140 is represented as a schematic electrical circuit further includes a plurality of monitors, preferably three, deployed throughout conduit 120, operative to safely monitor the fluid temperature in system 100. In one non-limiting example, the monitors may be tuned to about 38-39° C. A third monitor 184 measures the temperature at the end of conduit 120 before the fluid infusion to the patient. The three monitors are electrically connected in series.

Figure 5:
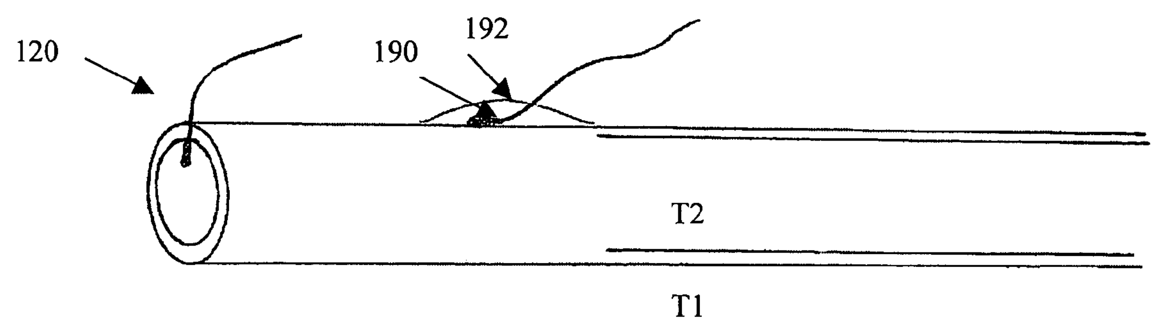

Reference is made now to FIG. 5 presenting another schematic and generalized illustration of the aforementioned conduit 120. A monitor 190 deployed on the external surface of conduit 120 regulates the temperature of conduit 120. An insulator 192 isolates monitor 190. The thickness of conduit 120 is configured such that the temperature of the external surface of conduit 120 is almost identical to the temperature of the internal wall conduit 120. In one non-limiting example, the temperature of the external surface of conduit 120 T1 is 37.2° C. and the temperature of the internal wall conduit T2 is 37° C. Another sensor 194 is placed directly inside the fluid path, and may be a temperature thermistor.

According to another embodiment of the present invention, system 100 is lightweight. In one non-limiting example, the weight of system 100 is about 1 Kg, in which the weight of heated conduit 120 is about 300 grams and the weight of the power source is about 700 grams. System 100 is hence lightweight and easy to handle in all weather and environmental conditions. System 100 is sterile and any parts coming in contact with the patient are disposable.

According to another embodiment of the present invention, system 100 is activated under a low voltage in the range of about 6V to 24V, preferably 12V.

According to another embodiment of the present invention, system 100 ensures a high stability under mechanical and thermal shocks.

According to another embodiment of the present invention, system 100 is adapted to be utilized in field environment such as emergency medical services, flight service, watercraft service or military because of the performance stability and the rugged configuration necessary for battlefield operation along with low power consumption.

The portability and ease of the invention enables more frequent warmed intravenous injection in the areas identified previously as well as expansion of warm intravenous injection into areas heretofore considered economically or technically unfeasible. These new areas include ambulances and military battlefield application.

In another embodiment, Emergency Medical Technicians, or military field hospital personnel, can activate beating system 100 while in areas remote from bulky materials facilities where time is critical.

According to another embodiment of the present invention, system 100 may be stored at temperatures between −20° C. to 55° C., preferably −20° C. to 40° C.

According to another embodiment of the present invention, the conduit life expectancy is about 5 years to about 10 years.

According to another embodiment of the present invention, system 100 further includes an insulator (not shown) surrounding metal conduit 120 operative to electrically insulate metal conduit 120 as well as to behave as a temperature insulator. Thus, conduit 120 is inexpensive, easy to manufacture, and is suitable for use in every field environment.

According to another embodiment of the present invention, system 100 further includes a monitor operative to determine the presence of a fluid flow and to interrupt the system operation if the fluid flow has been stopped.

All references cited herein are incorporated by reference in their entirety. Citation of a reference does not constitute an admission that the reference is prior art.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A device for heating a flow of liquid from an initial temperature to a desired temperature for intravenous delivery, the device comprising:

(a) an elongated metal conduit having an inlet for receiving the flow of liquid at the initial temperature and an outlet for delivering the flow of liquid at the desired temperature, said metal conduit being in direct thermal contact with the flow of liquid;

(b) at least one temperature sensing arrangement associated with said conduit and deployed to generate an output indicative of a temperature of the liquid at least one location along said conduit; and (c) a controller associated with said temperature sensing arrangement and deployed for generating electrical current flowing within at least one length of the wall of said metal conduit, thereby generating heat within said wall so as to heat the flow of liquid to reach the desired temperature at said outlet.

2. The device of claim 1, wherein said at least one temperature sensing arrangement includes a temperature responsive element positioned in thermal contact with an external surface of said conduit.

3. The device of claim 2, wherein at least part of said conduit has a wall thickness of no more than about 0.4 mm.

4. The device of claim 1, wherein said conduit is formed primarily from stainless steel.

5. The device of claim 1, wherein said temperature sensing arrangement includes a temperature responsive element deployed within the liquid flow in proximity to said outlet.

6. The device of claim 1, wherein said conduit is provided with a thermally insulating covering over a major portion of its surface.

7. The device of claim 1, wherein said conduit, said at least one temperature sensing arrangement and said controller are included within a portable housing.

8. The device of claim 7, wherein said housing further includes a battery associated with said controller and configured to allow operation of the device without connection to an external power supply.

9. The device of claim 1, wherein said controller is implemented as a reusable device, and wherein at least said conduit is implemented as a single-use interchangeable element.

10. The device of claim 1, further comprising a flow monitor associated with said controller and operative to sense the fluid flow through said conduit.

11. A device for heating a flow of liquid from an initial temperature to a desired temperature for intravenous delivery, the device comprising:

(a) an elongated metal conduit having an inlet for receiving the flow of liquid at the initial temperature and an outlet for delivering the flow of liquid at the desired temperature, said metal conduit comprising a metal wall that at least partially defines a liquid flow path from said inlet to said outlet, said metal wall being in direct thermal contact with said liquid flow path;

(b) at least one temperature sensing arrangement associated with said conduit and deployed to generate an output indicative of a temperature of the liquid at least one location along said conduit; and (c) a controller associated with said temperature sensing arrangement and deployed for generating electrical current flowing within at least one length of said metal wall, thereby generating heat by electrical resistive heating of the metal of said flow-path-defining wall so as to heat the flow of liquid to reach the desired temperature at said outlet.

* * * * *